United States Patent
Hengstler et al.

(10) Patent No.: US 11,152,116 B2
(45) Date of Patent: Oct. 19, 2021

(54) DISTRIBUTED NETWORK OF IN-VITRO DIAGNOSTIC DEVICES

(71) Applicant: Alverix, Inc., Franklin Lakes, NJ (US)

(72) Inventors: Stephan Hengstler, Campbell, CA (US); Tong Xie, San Jose, CA (US)

(73) Assignee: Alverix, Inc., Franklin Lakes, NJ (US)

( * ) Notice: Subject to any disclaimer, the term of this patent is extended or adjusted under 35 U.S.C. 154(b) by 0 days.

(21) Appl. No.: 16/917,619

(22) Filed: Jun. 30, 2020

(65) Prior Publication Data
US 2020/0335212 A1      Oct. 22, 2020

Related U.S. Application Data

(62) Division of application No. 15/657,449, filed on Jul. 24, 2017, now Pat. No. 10,706,966, which is a division of application No. 13/229,301, filed on Sep. 9, 2011, now Pat. No. 9,715,579.

(51) Int. Cl.
*G16H 40/67* (2018.01)
*G16H 10/40* (2018.01)

(52) U.S. Cl.
CPC .............. *G16H 40/67* (2018.01); *G16H 10/40* (2018.01)

(58) Field of Classification Search
CPC .................................. G06F 19/10; G06F 19/26
See application file for complete search history.

(56) References Cited

U.S. PATENT DOCUMENTS

| | | | |
|---|---|---|---|
| 6,136,610 | A | 10/2000 | Polito et al. |
| 6,440,066 | B1 | 8/2002 | Brady |
| 7,027,931 | B1 | 4/2006 | Jones et al. |
| 7,437,302 | B2 | 10/2008 | Haskell et al. |

(Continued)

FOREIGN PATENT DOCUMENTS

| | | |
|---|---|---|
| EP | 2787352 A | 10/2014 |
| WO | WO 2013/052318 A | 4/2013 |

OTHER PUBLICATIONS

IP Location Finder, "How to find Geolocation of an IP Address?" Nov. 1, 2010; downloaded from http://www.iplocation.net, 3 pages.

(Continued)

*Primary Examiner* — Mohammad K Islam
(74) *Attorney, Agent, or Firm* — Knobbe Martens Olson & Bear LLP

(57) ABSTRACT

A system is disclosed in which a plurality of in-vitro diagnostic (IVD) devices each include a network communication device for connecting to a publicly accessible data network. For example, IVD devices are provided with a cellular modem for connecting to a public cellular network. These IVD devices connect to the data network upon completion of a diagnostic test, and upload results of the test, as well as other appropriate data, to a remote device which is also on the network. The IVD devices also download appropriate data from remote network elements. The remote network element may be a network element such as a Hospital Information System (HIS) or Laboratory Information System (LIS) database. Alternatively, the remote device may be a remote server or another IVD device. This connectivity enables the system to accumulate diagnostic test data, and to analyze, report, and/or update the IVD devices based on the accumulated data.

16 Claims, 2 Drawing Sheets

(56) References Cited

U.S. PATENT DOCUMENTS

| | | | |
|---|---|---|---|
| 7,519,591 B2 | 4/2009 | Landi et al. | |
| 7,575,558 B2 | 8/2009 | Boecker et al. | |
| 7,651,841 B2 | 1/2010 | Song et al. | |
| 7,890,748 B1 | 2/2011 | Wyatt | |
| 8,007,999 B2 | 8/2011 | Holmes et al. | |
| 8,106,780 B2 | 1/2012 | Goodnow et al. | |
| 8,115,635 B2 | 2/2012 | Goodnow et al. | |
| 8,138,909 B2 | 3/2012 | Lewington et al. | |
| 8,223,021 B2 | 7/2012 | Goodnow et al. | |
| 8,257,654 B2 | 9/2012 | Maus et al. | |
| 8,260,392 B2 | 9/2012 | Say et al. | |
| 8,358,210 B2 | 1/2013 | Goodnow et al. | |
| 8,428,966 B2 | 4/2013 | Green, III et al. | |
| 8,606,593 B1 | 12/2013 | Green, III et al. | |
| 8,669,047 B2 | 3/2014 | Holmes et al. | |
| 8,737,971 B2 | 5/2014 | van Rooyen et al. | |
| 8,773,258 B2 | 7/2014 | Vosch et al. | |
| 9,459,200 B2 | 10/2016 | Dupoteau et al. | |
| 9,524,372 B2 | 12/2016 | Hengstler et al. | |
| 9,715,579 B2 | 7/2017 | Hengstler et al. | |
| 9,792,809 B2 | 10/2017 | Dupoteau | |
| 9,795,331 B2* | 10/2017 | Stafford | A61B 5/0015 |
| 10,180,417 B2 | 1/2019 | Hengstler et al. | |
| 10,458,972 B2 | 10/2019 | Hengstler et al. | |
| 10,706,966 B2 | 7/2020 | Hengstler et al. | |
| 2002/0059030 A1* | 5/2002 | Otworth | A61B 5/411 |
| | | | 702/19 |
| 2004/0167464 A1 | 8/2004 | Ireland et al. | |
| 2004/0249999 A1 | 12/2004 | Connolly et al. | |
| 2007/0016381 A1 | 1/2007 | Kamath et al. | |
| 2007/0081920 A1 | 4/2007 | Murphy et al. | |
| 2007/0184847 A1 | 8/2007 | Hansen et al. | |
| 2008/0024294 A1 | 1/2008 | Mazar | |
| 2008/0240983 A1 | 10/2008 | Harris | |
| 2009/0013311 A1 | 1/2009 | Ooba et al. | |
| 2009/0058635 A1 | 3/2009 | LaLonde et al. | |
| 2009/0058636 A1* | 3/2009 | Gaskill | A61B 5/349 |
| | | | 340/539.11 |
| 2009/0132204 A1 | 5/2009 | Bodlaender et al. | |
| 2009/0155921 A1 | 6/2009 | Lu et al. | |
| 2009/0163832 A1 | 6/2009 | Sunderani | |
| 2009/0192410 A1 | 7/2009 | Freeman et al. | |
| 2009/0271066 A1 | 10/2009 | Underdal et al. | |
| 2009/0292340 A1 | 11/2009 | Mass et al. | |
| 2010/0045789 A1 | 2/2010 | Fleming et al. | |
| 2010/0159599 A1 | 6/2010 | Song et al. | |
| 2010/0257027 A1 | 10/2010 | Greenberg et al. | |
| 2011/0053121 A1 | 3/2011 | Heaton | |
| 2011/0230743 A1 | 9/2011 | Inciardi et al. | |
| 2011/0291643 A1 | 12/2011 | Ravindran et al. | |
| 2011/0293153 A1 | 12/2011 | Plickert et al. | |
| 2011/0295078 A1 | 12/2011 | Reid et al. | |
| 2011/0295091 A1* | 12/2011 | Azer | G16H 40/60 |
| | | | 600/309 |
| 2012/0100557 A1 | 4/2012 | Fox et al. | |
| 2012/0112908 A1 | 5/2012 | Prykari et al. | |
| 2012/0232367 A1 | 9/2012 | Allegri et al. | |
| 2013/0018668 A1 | 1/2013 | Goldberg et al. | |
| 2013/0066562 A1 | 3/2013 | Hengstler et al. | |
| 2013/0066563 A1 | 3/2013 | Hengstler et al. | |
| 2013/0203620 A1 | 8/2013 | Glezer et al. | |
| 2013/0210163 A1 | 8/2013 | Hopwood et al. | |
| 2013/0281310 A1 | 10/2013 | Weidemaier et al. | |
| 2014/0228225 A1 | 8/2014 | Triener et al. | |
| 2014/0316732 A1 | 10/2014 | Dupoteau | |
| 2017/0175169 A1 | 6/2017 | Lee | |
| 2018/0137940 A1 | 5/2018 | Hengstler et al. | |
| 2019/0187139 A1 | 6/2019 | Xie et al. | |
| 2020/0132662 A1 | 4/2020 | Hengstler et al. | |

OTHER PUBLICATIONS

IP Location, How Do I find a geographical location from an IP Address?, http://www.iplocation.net, Nov. 15, 2010; 2 pages.
Martinelli, Nicole, "How Hospitals are Using the iPad", downloaded from http://www.cultofmac/com/64565/how-hospitals-are-using-the-ipad; Oct. 19, 2010, 4 pages.
The Free Dictionary, "Definition of Protocol", downloaded from http://www.thefreedictionary.com/p/protocol; Jul. 2014, 3 pages.
TÜV (Technischer Überwachungs Verein—Süd), "In vitro diagnostic devices directive—Understanding", (98/79/EC) 2008, in 9 pages.

* cited by examiner

DISTRIBUTED NETWORK OF IN-VITRO DIAGNOSTIC DEVICES

The present application is a divisional of U.S. patent application Ser. No. 15/657,449, filed on Jul. 24, 2017 and scheduled to issue as U.S. Pat. No. 10,706,966 on Jul. 7, 2020, which is a divisional of U.S. patent application Ser. No. 13/229,301, filed on Sep. 9, 2011 and issued on Jul. 25, 2017 as U.S. Pat. No. 9,715,579, entitled "DISTRIBUTED NETWORK OF IN-VITRO DIAGNOSTIC DEVICES." The contents of all of the above disclosures are hereby incorporated by reference herein.

BACKGROUND

Presently available in-vitro diagnostic (IVD) devices are used in various medical settings to detect the presence of numerous types of biological conditions, such as the presence of infection antibodies, quickly and reliably. Known IVD devices are used in hospitals, clinics, doctors' offices, and other patient care facilities to enable rapid detection and identification of potentially harmful conditions in patients presenting at these facilities.

One type of IVD device is configured to read or otherwise analyze lateral flow assays, which can test for a wide variety of medical and environmental conditions or compounds. For example, lateral flow tests can rely on a form of immunoassay in which the test sample flows along a solid substrate via capillary action. Known IVD devices can read lateral flow assay strips to detect the existence of a hormone, metabolite, toxin, or pathogen-derived antigen. This reading can be accomplished with the use of an imager, such as a CMOS imager or a CCD-based imaging device, which is configured to detect the presence or absence of a line on the lateral flow assay based on the presence or absence of a visual line on the assay. Some tests, implemented by IVD devices, are designed to make a quantitative determination, but in many circumstances the tests are designed to return or indicate a positive/negative qualitative indication. Examples of assays that enable such qualitative analysis include blood typing, most types of urinalysis, pregnancy tests, and AIDS tests.

Certain known IVD devices (including known assay test strip reader devices) are configured to report, store, and/or transmit diagnostic information determined solely resulting from a diagnostic test and not provided by a source external to the IVD device. That is, certain known IVD devices are configured to report, store, or transmit information related to the infection or other condition tested for, as well as to report, store, or transmit additional information manually entered by patient care personnel assisting in the use of the IVD devices. Some IVD devices are provided as stand-alone devices—that is, they perform infection detection by autonomously following a pre-programmed decision-making process or rule. For each test performed by such an IVD device, the same process is undertaken, and a result is generated in the same way. Moreover, in known IVD devices, a built-in or integrated display is used to display the results of the test, and the results may also be printed using a built-in or attached printer.

Many known IVD devices are not configured to send or receive data to or from any source external to the IVD device. In such devices, the only output enabled by the IVD devices is to display the results of a test on an integrated display. Certain other known IVD devices are configured to exchange data with another device, remote from the IVD device, through a short-range wired or wireless connection. For example, known IVD devices may exchange data with another device through a USB, serial, or proprietary wired connection, or through a Bluetooth, Wireless USB, or proprietary wireless connection. Finally, certain known IVD devices are configured to connect to a local area network (e.g., LAN) through a wired (e.g., Ethernet) or wireless (e.g., WiFi or ZigBee) connection.

Known IVD devices suffer from many drawbacks. First, known IVD devices suffer from drawbacks in that any data used by known IVD devices to generate outcomes or test results must either be determined by the device as a part of the analysis of the test results, or must be manually entered by medical personnel or other users of the IVD device. This manual entry is frequently limited, and involves the use of a keyboard or a barcode scanner. Even if such data is manually entered, known IVD devices suffer from drawbacks in that the correctness of the entered data is questionable, and in fact may be in jeopardy, depending upon the mechanism for entering data and/or the care given to the correct entry of data by the user of the IVD device. Finally, known IVD devices suffer from drawbacks in that they are limited to receiving and utilizing only that data and/or information known to the individual entering the information into the device. Other information (such as information obtainable from medical or other databases or information repositories, or from a device manufacturer) is not available for use by the IVD device in generating its results.

Further, known IVD devices suffer from drawbacks in that the limited connectivity options provided with such IVD devices prevents the devices from forming ad-hoc networks and connecting directly to other IVD devices or network elements. To the extent that network capabilities are provided, data generated by IVD devices is limited to transmission within a given patient care facility. Moreover, a patient care facility which enables connection of IVD devices to a network must operate an appropriate LAN or other network, and must provide infrastructure for integrating and maintaining IVD devices within the network, both of which can be costly endeavors. Finally, even with known network-enabled IVD devices, manual interaction is required to access the test results generated by an IVD device and to store it electronically in an appropriate medical facility database. For example, manual intervention is required in known IVD devices to upload data indicative of an outcome of a diagnostic test from an IVD device and store it in an appropriate Hospital Information System (HIS) or Laboratory Information System (LIS) database.

Known IVD devices do not provide a mechanism to enable near-patient testing results to be provided to a centralized server for analysis, aggregation, and distribution using an established public network, such as a public telephone network. Moreover, known IVD devices do not provide a mechanism by which a centralized server can track, manage, and determine characteristics of those IVD devices to ensure appropriate use of the devices and appropriate use of environmental data detected by the IVD devices.

Thus, it is desirable to create IVD devices that are configured to receive and store data from sources external to the individuals utilizing the IVD devices, in addition to data currently gathered by known IVD devices, and to utilize the data received from external sources to supplement the analysis capabilities of the IVD device, such as by confirming or verifying part of the diagnostic information generated by the IVD device. It is further desirable to create IVD devices that are network-ready, such that the devices can connect to a network (such as the Internet) and obtain external data independent from the actual test being performed. It is also desirable to create an IVD device that is capable of sending or uploading data to a remote repository via a network, such that data about the tests performed with such IVD devices can be stored and analyzed, alone or in the aggregate, by remote devices or personnel. Finally, it is desirable to provide an IVD device that includes a built-in mechanism for accessing publicly available networks, such as telephone or cellular networks, to enable direct communication by the IVD device with network elements or other IVD devices to enable electronic test result transmission, storage, analysis and/or dissemination without requiring separate intervention or action by the user of the IVD device.

SUMMARY

The present disclosure relates to a system, method, and apparatus for providing enhanced results of known diagnostic tests by augmenting the information used to generate the results of such tests.

The disclosed system facilitates the transmission of information following the collection of that information in diagnostic examination, such as diagnostic information collected using diagnostic instruments or tests. The disclosed system advantageously focuses on the transmission of information to individuals that most need that information, as opposed to simply focusing on the collection of that information. For example, when one or more diagnostic tests are performed outside of a laboratory or other medical environment, the disclosed system enables the transmission of the results of those diagnostic tests to devices and/or users that consume the data, such as by analyzing or storing the data in a database.

Furthermore, the disclosed system advantageously enables laboratories and other medical facilities that lack the requisite information transmission infrastructure to transmit data to appropriate, necessary consumers. Thus, for example, if a relatively rural laboratory or facility does not contain network infrastructure, the disclosed system nonetheless enables that laboratory or facility to transmit information to an end-user for analysis, storage, or other consumption. In various embodiments, discussed below, the disclosed system enables this functionality by relying on publicly accessible, established data transmission networks, such as cellular telephone networks.

In various embodiments, however, the disclosed system facilitates transmission of results from a testing site (such as from a testing device) to a private, centralized server. The server may then distribute the information it has received as appropriate, such as by distributing the information to testing centers, primary care physicians, individuals, insurance companies, or other appropriate recipients of the data. In one embodiment, the centralized server performs at least some aggregation and/or analysis of the data prior to distribution. For example, if a patient has a cardio-monitor in his or her home, the data from the cardio-monitor may be transmitted to the server via a public cellular infrastructure, and the central server may then aggregate the data for submission to the individual's primary care physician once a week.

In some embodiments, the server performs additional functions. For example, the server may apply rules to data, may encrypt and/or decrypt data, may track transmitting devices (including the environmental conditions of those transmitting devices), may maintain a registry of devices, and may perform other tasks as appropriate and as discussed in more detail below.

For example, in a known in-vitro diagnostic (IVD) device, the instant disclosure relates to a mechanism by which the standard, conventional test results are enhanced or expanded by providing the IVD device with additional information or data from which to determine test results, or to store in association with the test results to enable in-depth analysis of the test results. This additional information may be automatically received from a network or other external source, and may be used to aid in confirmation and verification of the diagnostic information generated by the IVD device. In the event the data is received from a network or external source, the IVD device in one embodiment may include a device, such as a cellular modem, to enable the IVD device to connect with a publicly available and publicly maintained data network, such as a public telephone or cellular network. Alternatively or in addition, diagnostic test data obtained by the IVD device can be tagged with hardware and/or environmental information to enable accurate analysis and aggregation of data based on tests performed with or by the IVD device. For example, the diagnostic test data can be tagged with device quality data, device lifetime data, environmental temperature data, and the like.

In an embodiment of the disclosed system, a diagnostic data generation device, such as an IVD device, is configured to generate a test result or other diagnostic data based on a biological sample. For example, an IVD device is configured to analyze the results of a lateral flow assay test by analyzing whether certain reactions occur along the length of a lateral flow assay test strip when the strip is brought into contact with a biological sample. In addition to the biological sample (and the data obtainable therefrom), the disclosed IVD device is configured to receive additional information, from which additional conclusions and/or analyses can be drawn with regard to the test. Examples of this additional information usable by an IVD device as disclosed herein include diagnostic information specific to the IVD device or the test itself, network information relating to the network to which the IVD device is connected, environmental data about the environment in which the IVD device was created, stored, or used, or other suitable additional information to enable augmentation of the test results generated by the IVD device.

In one embodiment, the additional information is provided automatically (i.e., without a user of the IVD device requesting it) via a network connection. In one such embodiment, each IVD device includes a device, such as a cellular modem, for accessing a publicly provided, publicly maintained data network. The publicly provided network could be a public telephone network, a public cellular network, or another suitable kind of publicly available data network. In one embodiment, the disclosed IVD device is configured to receive additional information via a network, such as a Local Area Network or a cellular network, and is further configured to use this additional information to generate further or more detailed test results. This additional information may relate to the specifics of the network to which the IVD device is connected (e.g., the IP address of the IVD device on the network), or may relate to specific characteristics of the IVD device on which the diagnostic data was generated (e.g., the storage temperature of the IVD device). Alternatively, the additional information usable by the IVD device to augment or enhance its test results may be input by the user of the IVD device and/or by a health care professional or other individual remote from the IVD device.

Upon receiving the additional information, the IVD device of one embodiment is configured to utilize the received information in combination with the diagnostic information generated by the IVD device itself. Hardware and environmental information may be used to ensure quality and integrity of the diagnostic test result. For example, the IVD device may utilize data about the temperature at which it was stored to validate or confirm the results of the performed diagnostic test. Alternatively or in addition, the disclosed IVD device may upload or otherwise provide both the data indicative of the diagnostic test result and the additional information to a remote network element, such as a Hospital Information System (HIS), a Laboratory Information System (LIS), or over an ad-hoc network to another IVD device for aggregation and further analysis, as discussed in detail below. This sharing of data via publicly maintained data networks enables known IVD devices to provide accurate results, enables the disclosed system to perform analyses on aggregations of real-time data from a plurality of IVD devices, enables IVD devices to be calibrated on-the-fly, and enables tests themselves to be calibrated or enhanced based on real-time results, thus advantageously enhancing the effectiveness of tests enabled by such IVD devices and the utility of data generated by such IVD devices.

It should thus be appreciated that one embodiment of the disclosed system and methods enable IVD devices to obtain and utilize independent and additional data to further augment the results of tests performed by the IVD devices. This additional data may be external to the test itself and/or to the facility at which the test is performed, and may be provided to the IVD device via a network or based on the environment of the IVD device. The external data may be advantageously used for many purposes, including complementing or confirming the diagnostic information generated by the IVD device.

It should be further appreciated that one embodiment of the disclosed system and methods enable IVD devices to connect to certain network infrastructure elements over one or more publicly provided data networks, such as a cellular network, using a built-in connection device. Such network connectivity enables IVD devices to automatically communicate diagnostic test data, as well as additional data determined by the IVD device itself or via the connection to the data network, to certain network elements for aggregation, analysis, and reporting. This augmented set of data further enables IVD devices themselves, as well as criteria and protocols for performing tests, to be updated on-the-fly, and enables real-time analysis of large sets of IVD data.

Additional features and advantages are described herein, and will be apparent from, the following Detailed Description.

DETAILED DESCRIPTION

Figure 1A:
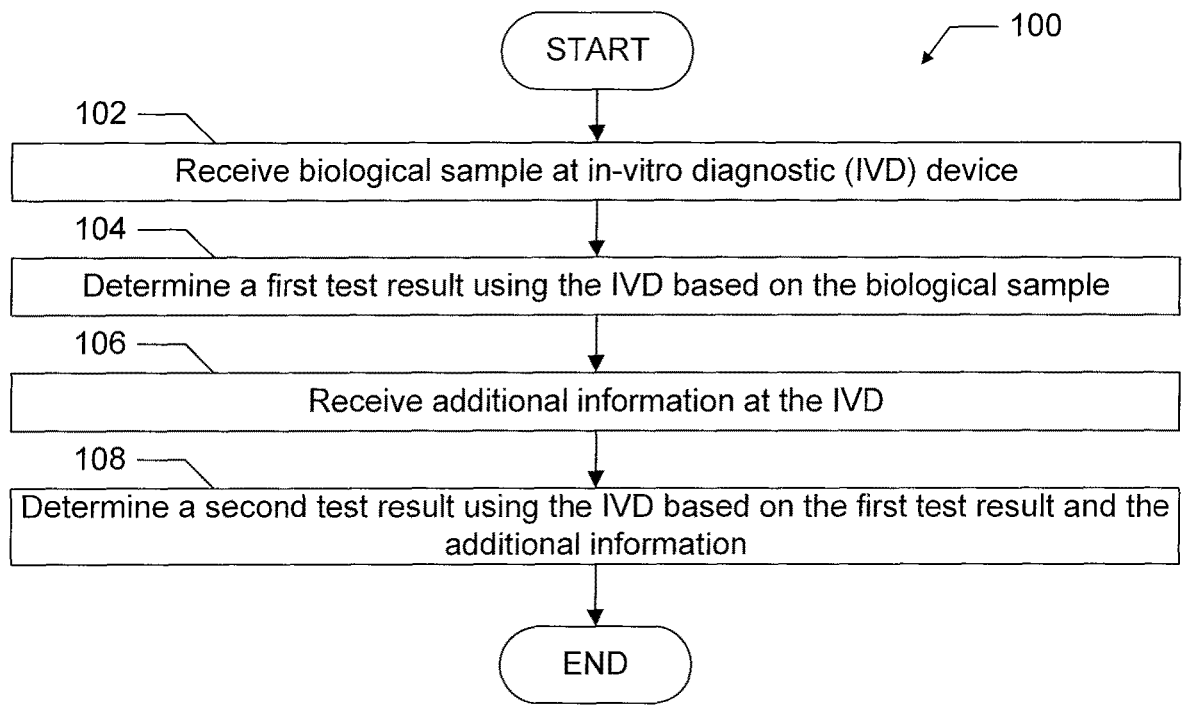
FIG. 1A is a flow chart of an example process for providing an in-vitro diagnostic (IVD) device with additional information for use in generating results of a test, as disclosed herein.

The present disclosure relates generally to in-vitro diagnostic (IVD) devices, the information made available to such IVD devices, and the results generated by such IVD devices. More particularly, one embodiment of the present disclosure relates to IVD devices which are configured to determine a results of a diagnostic test, such as a diagnostic test performed on a biological sample using a lateral flow assay test strip. In this embodiment, an IVD device is configured to receive additional information beyond the information obtainable by analyzing the biological sample (e.g., beyond the determination that one or more lines was displayed on a lateral flow assay), such as by receiving additional input from a user or by receiving additional information over a network, and to use this additional information to determine an additional result of the diagnostic test. Another embodiment of the present disclosure relates to IVD devices that are configured to communicate with remote devices, such as other IVD devices or other remote network elements and data repositories, to exchange data with the remote devices for enhancing the results otherwise determinable by the IVD devices. In a further embodiment, the IVD device includes a network access device, such as a cellular modem or other appropriate access device, which enables the IVD device to access a public data network such as a public telephone or cellular network. In this embodiment, certain additional data may be obtained through the data network, and the disclosed IVD device may automatically upload diagnostic data and any determined additional data to a remote network element via the data network, as described in detail below.

The instant disclosure is applicable in the context of IVD devices generally, many different kinds of which are known in the art. For example, the instant disclosure is applicable to IVD devices that are configured to read lateral flow assay test strips, such as by detecting the presence or absence of visible or other lines on the assay test strips following application of a biological sample to the assay test strip. The instant disclosure is also applicable in the context of IVD devices that analyze the results of reactions occurring in a test tube or other controlled environment, in which a biological sample such as a bodily fluid reacts with a reagent or other substance to generate a chemical reaction. While at various points throughout this disclosure assay test strip reader IVD devices are discussed, it should be appreciated that any suitable IVD device, such as IVD devices frequently used in hospitals, clinics, doctors' offices, or other patient care facilities for rapid detection of various infections, can equally make use of the concepts disclosed herein.

In one embodiment of the disclosed system, an IVD device is configured to determine an outcome of a diagnostic test in much the same way as with conventional IVD devices. That is, the IVD device is configured to determine an outcome of a diagnostic test by analyzing a biological or other kind of sample (or a reaction therewith) applied to the IVD device. In this embodiment, however, the IVD device is configured to perform or enable additional analysis to be performed beyond the diagnostic test. That is, the IVD device is configured to receive additional information or data, which additional information or data can be combined with the results determined by the IVD device based on the biological sample, to generate an additional or augmented result of the diagnostic test. In one embodiment, this additional or augmented result includes a result which confirms or verifies part of the result of the diagnostic test determined by the IVD device's analysis of the biological sample. This additional data, as well as the additional results enabled thereby, are discussed in detail below.

In another embodiment, the disclosed IVD device is configured to connect to one or more existing networks to facilitate the exchange of information between the IVD device and a remote device, such as a remote IVD device or some other kind of remote network resource. In an example of this embodiment, an IVD device is equipped with one or more devices, such as a cellular modem, to enable connection with remote network elements over publicly accessible networks, such as a public telephone network or a cellular network. Such an IVD device may thus communicate over the existing network without relying on intermediate, short-range links or connections, such as Bluetooth, UART, USB, WiFi, Wireless USB, ZigBee, or the like.

By enabling connection via existing networks as described, one embodiment of the disclosed IVD device enables the transmission, storage, dissemination, and analysis of electronic test results and other data related to the IVD devices without requiring a user to physically connect the IVD device to a suitable network hub or element. In one embodiment, the disclosed IVD device is configured to communicate, via the disclosed network, in a wireless fashion, without a short-range link, in a two-way fashion with at least one network element.

In still another embodiment, the disclosed IVD device is configured both to determine an additional or augmented test result and to communicate with one or more remote network devices over an existing network. In this embodiment, an IVD device enables a user to perform a diagnostic test, as described, and thereafter to communicate via an existing network with a remote device, such as a remote IVD device or another remote network resource. Over the communication link established using the existing network, the IVD device receives information usable to determine the additional or augmented test result. In one embodiment, the additional or augmented test result is determined by the IVD device upon the IVD device receiving additional information. In another embodiment, the additional or augmented test result is determined by a remote network element, such as a remote IVD device or a remote server, upon the IVD device sending the diagnostic information determined based on the biological sample to the remote network element.

In one embodiment, the additional result enabled by the disclosed IVD devices includes a confirmation or verification of the results of a diagnostic test performed by the IVD device. For example, information obtained by the IVD device may confirm that at a given operating condition, a designated raw data result (e.g., a designated detected voltage) corresponds with the determined result of the diagnostic test. In another embodiment, the additional result enabled by the disclosed IVD devices includes storage of certain data, such as environmental data, in association with a particular test result. This storage of data in association with a test result enables the disclosed IVD device (or a network element to which the IVD device transmits data) to construct aggregate analyses or reports of data from a plurality of different diagnostic tests.

FIG. 1A illustrates a flow chart of a process 100 for operating an IVD device according to one embodiment disclosed herein. Although the example process 100 is described with reference to the flow chart illustrated in FIG. 1A, it should be appreciated that many other processes of operating an IVD device are contemplated. For example, the order of certain of the steps of process 100 may be changed, and certain of the steps of process 100 are optional.

According to FIG. 1A, an IVD device is operated by first receiving a biological sample in the IVD device, as indicated by block 102. For example, if the IVD device is a device configured to read a lateral flow assay strip, the process 100 may include receiving a biological sample, such as urine or another bodily fluid, on an appropriate assay test strip. Upon receiving the biological sample, the disclosed IVD device determines a first test result based on the received biological sample, as indicated by block 104. For example, if a bodily fluid was applied to a lateral flow assay test strip, the IVD device may determine a result of the diagnostic test, such as whether a person who provided a urine sample is pregnant, by analyzing whether certain lines or other physical indicia are present on the lateral flow assay test strip following application of the biological sample thereto. It should be appreciated that determining the first test result could be performed according to any one of a number of known diagnostic tests enabled by known IVD devices.

After the IVD device determines the first test result, as indicated by block 104, the IVD device receives additional information, as indicated by block 106. This additional information may be diagnostic information, network information, hardware information, environmental information, or other appropriate additional information as described herein. Using both the additional information and the first test result previously determined by the IVD device, the IVD device determines a second test result, as indicated by block 108. For example, if the first test result includes diagnostic information, the IVD device may use the additional information in conjunction with the first test result to verify or confirm the diagnostic information represented by the first test result.

Figure 1B:
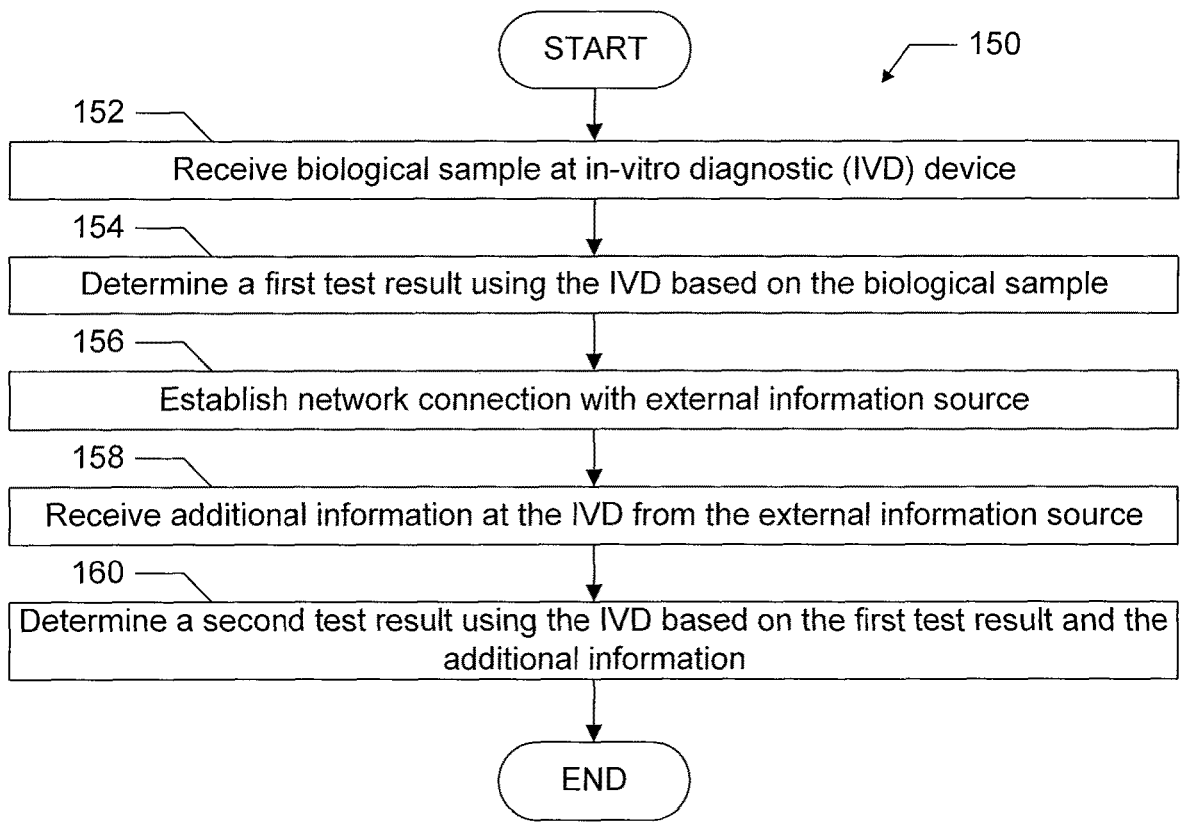
FIG. 1B is a flow chart of an alternative example process for providing an in-vitro diagnostic device with additional information via a network connection for use in generating results of a test, as disclosed herein.

FIG. 1B illustrates a flow chart of an alternate process 150 for operating an IVD device according to one embodiment disclosed herein. Although the example process 150 is described with reference to the flow chart illustrated in FIG. 1B, it should be appreciated that many other processes of operating an IVD device are contemplated. For example, the order of certain of the steps of process 150 may be changed, and certain of the steps of process 150 are optional.

According to FIG. 1B, as in FIG. 1A, an IVD device is operated by first receiving a biological sample in the IVD device, as indicated by block 152. Upon receiving the biological sample, the disclosed IVD device determines a first test result based on the received biological sample, as indicated by block 154.

In the process 150 illustrated in FIG. 1B, the IVD device then establishes a network connection with an external information source. For example, the IVD device may establish a network connection over a public telephone or cellular network using a built-in cellular modem or other network access device. The IVD device may then establish such a connection with a remote IVD device, a remote server, or another remote network element or resource. Upon establishing the connection, the IVD device receives additional information from the external information source, as indicated by block 158. For example, if the IVD device establishes a connection with a remote database accessible from a remote server via a network connection, the IVD device receives information from the database, which information is usable to further analyze the results of the diagnostic test. Finally, the IVD device determines a second test result based both on the first test result and the additional information received from the external information source, as indicated by block 160. As described above with respect to FIG. 1A, an example of this determination may include a verification of the first test result using information obtained from a remote network resource, such as from a remote server or from a remote IVD device.

In various embodiments, the disclosed IVD device is configured to generate or otherwise access diagnostic information for use during the diagnostic test. In one embodiment, diagnostic information (that is, the information obtained by the IVD device directly) is inherent to the IVD device, determined during the course of a test, or manually entered by patient care personnel through the use of a keyboard, barcode scanner, or other input device. Examples of this diagnostic information include the serial number of an IVD device (such as programmed by a device manufacturer), the date and/or time of a test (which can be manually entered or provided by a real-time clock of the IVD device), the location of the test (such as the name of the patient care facility at which the test was performed), a patient identifier associated with the patient, the test type (such as the type of infection tested for), the test result (e.g., positive or negative), the diagnosis as determined by the patient care personnel, the prescribed treatment or medication as determined by the patient care personnel, and any other additional test or patient information pertinent to the test performed by the IVD device.

In one embodiment, the disclosed IVD device is configured to receive information in addition to diagnostic information, which additional information is usable to generate the additional result. For example, the IVD device may receive additional diagnostic information from a remote device via a network connection, or may receive additional diagnostic information from a user of the IVD device. If the user of the IVD device provides the additional diagnostic information, the information may be input to the IVD device via a keyboard, a barcode scanner, or another suitable input device.

In one embodiment, an IVD device is configured to receive additional information that is independent of and external to the IVD device itself. For example, this additional information may be network information, hardware information, or environmental information, which in one embodiment complements the diagnostic information obtained by the IVD device.

In one embodiment, the disclosed IVD device is configured to utilize network information in conjunction with the diagnostic information to augment or otherwise enhance the results of the diagnostic test performed by the IVD device. In various embodiments, this network information includes the subscriber number of the IVD device (such as an identification number assigned to the IVD device by a public network on which the IVD device is communicating), the date and time of the test (as determined by the public network based on the date and time of connection to the network), the geographical location of the test (as determined by the location of the IVD device at the time of connection or communication over the network), the IP address of the IVD device on the network, or other information pertinent to the network on which the IVD device is communicating.

In one embodiment, the disclosed IVD device is configured to utilize hardware or environmental information in conjunction with the diagnostic information and/or the network information to augment or otherwise enhance the results of the diagnostic test provided by the IVD device. In various embodiments, this hardware or environmental data includes device quality data, calibration date and data, environmental temperature, humidity, or other characteristics (during manufacture, storage, or the test itself), or other suitable hardware and environmental data.

In various embodiments, the disclosed IVD device is configured to combine certain determined additional data with the results of the test determined by the IVD device to augment or enhance the test results generated by the IVD device. For example, the IVD device in one embodiment combines the results of a test (e.g., a determination about the presence of certain visible lines on an assay test strip) with additional data (e.g., configuration data) to determine a more precise result of the test enabled by the IVD device. For instance, if the presence of a line on an assay test strip indicates the presence or absence of a condition, and the intensity of the line indicates the severity of the condition, the calibration data received by the IVD device may enable the IVD device to make a determination as to the intensity of the line, and thus the severity of the condition, whereas a prior art IVD device may have only been able to determine the presence of the line. Thus, it should be appreciated that in one embodiment, the disclosed IVD device enables augmentation of test results to determine more detailed, useful, or complete results than were previously possible.

In another embodiment, the IVD device combines the additional data with the test results determined by the IVD device and enables storage, reporting, transmission, or other analysis of the combined results. For example, if the disclosed IVD device is configured to analyze an assay test strip, the time and/or date may be stored in association with a particular test, and thereafter communicated via a network connection to a remote repository, to enable further analysis of the test result/time and date combination. Such an IVD device may enable analysis of the development of a condition over time, wherein if a first result occurs on a first day and a different second result occurs on a second day following the first day, the difference in test results can be correlated with a passage of time and can thus be utilized to track the progression of a condition.

In one embodiment, the disclosed IVD device advantageously enables the collection of and association of test results with additional data which does not need to be input by the patient, medical care professional, or other user of the IVD device itself. It should be appreciated that this capability both reduces the burden on the user of the IVD device and also increases the reliability of the data collected and relied on by the IVD device.

In another embodiment, wherein the disclosed IVD device is configured to create an ad-hoc network with another IVD device, the system enables a non-functional IVD device to provide valid and usable test results even in the absence of correct functioning. For example, if a first, non-working IVD device is capable of determining data indicative of a result of a test (e.g., a voltage detected by a sensor when positioned adjacent to an assay test strip) but is not capable of determining what that voltage means, the voltage itself can be provided to another, functional IVD device via an ad-hoc network connection with that functional IVD device. Upon providing the data, the functional IVD device can analyze the data and send its analysis back to the non-functional IVD device, or can upload and store the data in a remote repository, such as a network server. Thus, the disclosed system enables IVD devices to create ad-hoc networks to ensure proper functionality as much of the time as possible.

In one embodiment, data collected by the IVD device can be seen as being tagged with external data which is automatically determined, and which does not depend on an operator for entry. For example, diagnostic test data determined by an IVD device can be seen as being tagged with hardware and/or environmental information, such as device quality data, device lifetime data, environmental condition data, and the like. Thus, the disclosed IVD devices may obtain and utilize independent and external data, in addition to data generated by the IVD device as a part of the diagnostic test and/or information provided by a user of the IVD device, from a network source, based on the IVD device's hardware, and/or from its environment. This network, hardware, and environmental data may complement, confirm, or enhance the diagnostic data captured by the IVD device.

In various embodiments, the disclosed IVD device is configured to communicate with another device (either another IVD device or a network element such as a remote server) via an appropriate network. In one such embodiment, the disclosed IVD device is configured to communicate via a public telephone network, a public cellular network, or a global positioning system (GPS). As discussed above, the network through which the IVD device communicates may provide certain information which is combined with the diagnostic information, such as information about the geographical location of the IVD device or information about the date and time of the test. The network connection may also be an appropriate telemetric connection as is described in detail below.

In various embodiments, one or more IVD devices are equipped with a device to enable a telemetric connection over one or more publicly accessible or available networks. In such embodiments, IVD devices are not limited to being standalone devices, capable only of displaying data on local display devices, and are not limited to devices which must be specially coupled with the remote facility to which they will connect. Rather, IVD devices equipped with a device to enable telemetric connections advantageously enable such IVD devices to communicate test results and other data directly to a facility outside the point of care facility, enable the IVD devices to link directly with other IVD devices, enable the easy integration of IVD devices without concern for the capabilities of a specific network of IVD devices, and enable automatic uploading and sharing of data with a Hospital Information System (HIS), Laboratory Information System (LIS), or other suitable network-accessible repository. It should be appreciated that through the use of openly accessible, standardized, and globally available networks, the disclosed system enables the automatic transmission of electronic test result information, as well as the storage, analysis, and dissemination of such information, in a form transparent to the user and without requiring any user interaction.

In various embodiments, the disclosed system enables one or more IVD devices to communicate with a remote device, such as another IVD device or a remote network element, via one or more publicly implemented and maintained networks. In one embodiment, an IVD device configured to so communicate over a network connection includes a network access device, such as a cellular modem, to facilitate such access. In various embodiments, the disclosed system may enable communication over public networks such as 2G, 3G, or beyond 3G public cellular networks, may operate under CDMA, W-CDMA, GSM, IMT-2000, PCS, or other cellular communication protocols, or may communicate over another suitable publicly accessible network.

Figure 2:
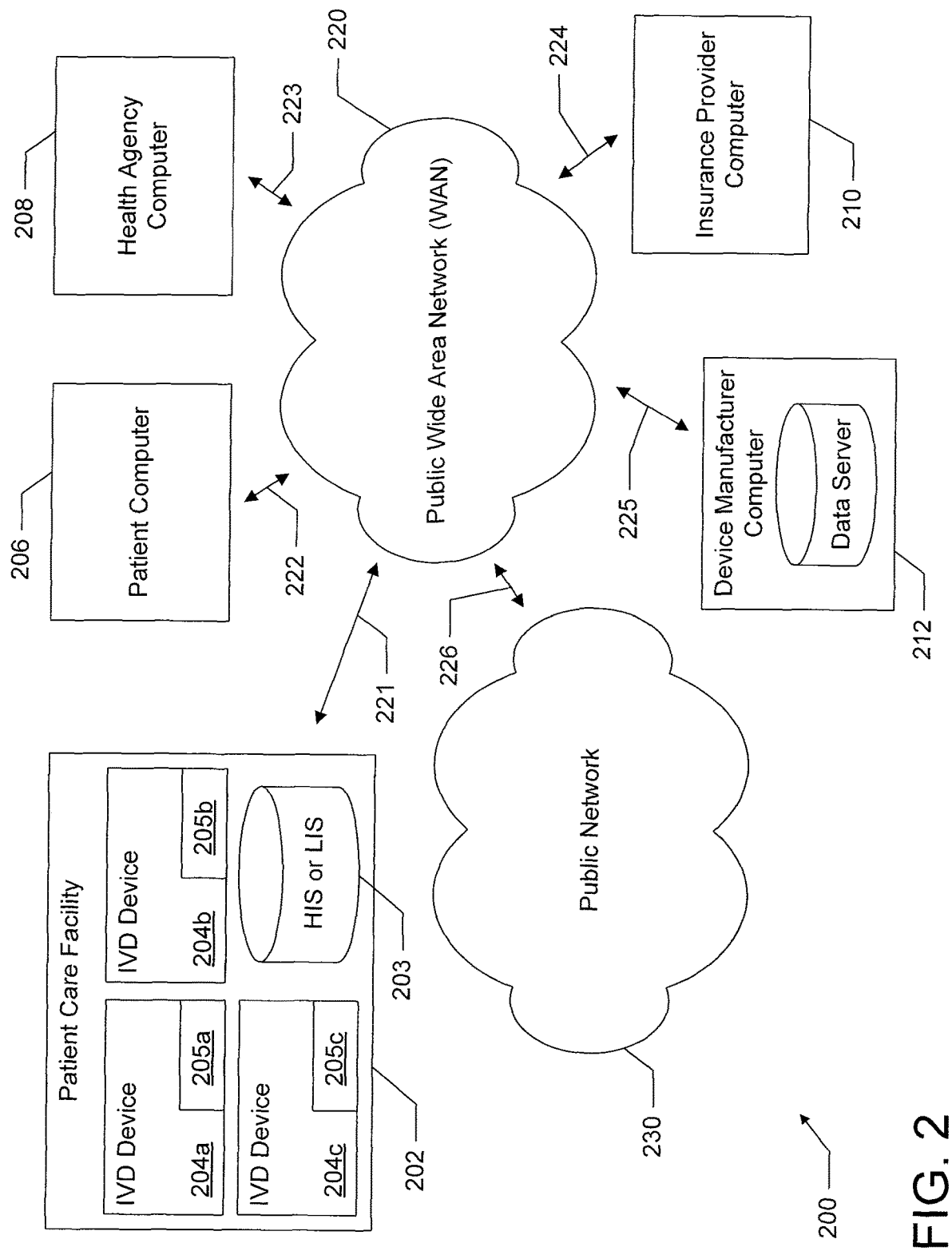
FIG. 2 illustrates a schematic block diagram of an example data network, to which a disclosed IVD device can connect, which enables the IVD device to communicate data obtained as a result of a diagnostic test and/or automatically obtained data in addition to the diagnostic test data, with various remote network elements, for aggregation, analysis, reporting, and feedback generation, as disclosed herein.

Referring now to FIG. 2, a schematic illustration of one networked embodiment of the disclosed system 200 is illustrated. In the illustrated embodiment, arrows between certain devices and either the Public Wide Area Network (WAN) 220 or the Public Network 230 indicate that such devices are configured to engage in two-way communication via such a network. For example, if a network element illustrated in FIG. 2 is associated with an arrow pointing to the network element and the Public Network 230, that device is configured to both send data to another device via the Public Network 230 and to receive data from another device via the Public Network 230.

FIG. 2 illustrates an example schematic representation of a patient care facility 202. The patient care facility 202 illustrated in FIG. 2 may represent a patient facility, such as a hospital, doctor's office, or clinic, at which one or more diagnostic tests is applied or given to a patient. In the illustrated embodiment, the patient care facility 202 is shown as including or encompassing a Hospital Information System (HIS) or Laboratory Information System (LIS) database 203. That is, in the illustrated embodiment, the patient care facility 202 maintains or otherwise provides access to an HIS or LIS database 203. In the illustrated embodiment, the HIS or LIS database 203 is a repository for test results, summary reports, or other data related to patients utilizing the patient care facility 202. In various embodiments, the HIS or LIS database 203 is additionally coupled with one or more processors (not shown) for performing certain processing tasks, such as analysis of data stored in the HIS or LIS database 203.

In the illustrated embodiment, the patent care facility 202 also includes a plurality of IVD devices 204a, 204b, and 204c. In one embodiment, the IVD devices are diagnostic test devices, such as devices for reading assay test strips, that are configured to determine diagnostic test result information based on a provided biological sample. It should be appreciated that any suitable IVD device could be advantageously used concurrently with the disclosed system.

As further illustrated in FIG. 2, each IVD device 204a, 204b, and 204c includes a network communication device 205a, 205b, or 205c, respectively. For example, the network communication devices 205a, 205b, and 205c could be cellular modems or other devices configured to communicate with a public network such as the Public Wide Area Network 220 or the Public Network 230. In one embodiment, the network communication devices 205a, 205b, and 205c enable the respective IVD devices to communicate with either one another, or with another network element, as disclosed herein. In addition, in one embodiment, the network communication devices 205a, 205b, and 205c enable the respective IVD devices to communicate data indicative of diagnostic test results to remote resources, such as the HIS or LIS database 203 for storage and/or further analysis.

The system 200 of FIG. 2 indicates, by arrow 221, that the patient care facility 202 (and the IVD devices/HIS or LIS database contained therein) are configured to communicate via Public Wide Area Network 220. In one embodiment, one or more of the Public Wide Area Network 220 and the Public Network 230 limits, at least in part, access to the network. Moreover, in one embodiment, the disclosed system 200 enables communication between the patient care facility by encrypted or other secure data transmission protocols, as described below.

System 200 also includes a patient computer 206, health agency computer 208, insurance provider computer 210, and device manufacturer computer 212. Each of these network elements are able to communicate with one another and with the patient care facility 202 via the Public Wide Area Network 220, as indicated by arrows 222, 223, 224, and 225, respectively. Arrow 226 indicates that the Public Wide Area Network 220 can communicate with a Public Network 220 of another type, such as the Internet. Thus, the devices illustrated in FIG. 2 are configured to communicate with one another either via Public Wide Area Network 220, Public Network 230, or some combination thereof.

In the illustrated embodiment, each of the computers enables a different party to communicate with the device manufacturer server 212 and the IVD devices 204a, 204b, 204c and HIS or LIS database 203 contained therein. For example, the patient computer 206 enables patients to communicate with the device manufacturer computer 212, the health agency computer 208 enables one or more health agencies to communicate with the patient care facility 202, the insurance provider computer 210 enables an insurance provider to communicate with the patient care facility 202, and the device manufacturer computer 212 enables the manufacturer of the IVD devices to communicate with the patient care facility 202. It should be appreciated that in the illustrated embodiment, the device manufacturer computer 212 enables the IVD devices 204a, 204b, and 204c to communicate with a data server 212a coupled to the device manufacturer computer 212 to, among other things, receive necessary data, such as calibration data, firmware, or other software and data upgrades, when the need arises.

In various embodiments, the network 200 of FIG. 2 enables the transmission and exchange of data including test results and additional data sent along with the test results. For example, the data transmitted among the various network elements of the system 200 could include diagnostic data and information, network information, hardware information, and environmental information as described above. In one embodiment, some or all of the data transmitted among the various elements of the illustrated system 200 are encrypted to prevent unwanted access to the transmitted data. In addition to protecting the data from interception and unwanted consumption, this encryption may also validate or maintain the integrity of the transmitted data, such as by providing a checksum or other mechanism to ensure that all transmitted data was received.

In one embodiment, the patient computer 206, health agency computer 208, insurance provider computer 210, and device manufacturer computer 212 are standard desktop or laptop computers accessible by the appropriate party. In another embodiment, one or more of the patient computer 206, health agency computer 208, insurance provider computer 210, and device manufacturer computer 212 are mainframe or server computers configured to handle large quantities of data and/or to provide complex processing and analysis routines. In this embodiment, the appropriate entity which is responsible for the illustrated computer device (e.g., the insurance company responsible for the insurance provider computer) can access some or all of the data uploaded from the IVD devices and stored within the system, depending on the purpose of the user's access. For example, an insurance company may access certain test data to verify that a particular insured individual does in fact have the ailment for which a claim was filed, or to verify that treatment for an ailment is ongoing. It should be appreciated that in various embodiments, entities other than those of the illustrated network elements in FIG. 2 may be able to access the data uploaded by the IVD devices as necessary to perform those entities' respective tasks.

In another embodiment, one or more of the patient computer 206, health agency computer 208, insurance provider computer 210, and device manufacturer computer 212 are portable computers, such as personal digital assistants (PDAs) or cellular telephones, which are configured to enable users to access data from a handheld, portable device. In such embodiments, the processing capabilities of the portable devices may be somewhat limited; as a result, portable devices may be primarily intended to enable users to access data as opposed to performing complex processing, reporting, or other analysis on the data. In one embodiment, not shown, one or more medical professionals such as health care personnel staffing the patient care facility 202 access data communicated by the IVD devices 204a, 204b, or 204c using an appropriate handheld device, such as a PDA, cellular telephone, or other handheld, portable device. In this embodiment, appropriate health care personnel can have access to, or be actively made aware of, patient data immediately upon the patient subjecting himself or herself to a diagnostic test using an IVD device.

The network architecture illustrated in FIG. 2 enables IVD devices to transmit, store, analyze, and disseminate electronic test results and summaries over known and already-implemented publicly accessible networks. Moreover, in instances in which analysis to be performed is either dependent upon data in the aggregate (i.e., from a plurality of IVD devices), or is too processor-intensive to be performed in an individual IVD device, the disclosed system enables IVD devices to transmit appropriate data to a central location, such as an HIS or LIS database, and enables relatively powerful processors at the central location to efficiently process and analyze the data. Finally, the disclosed system, as illustrated in FIG. 2, enables software updates to be pushed out to IVD devices from a device manufacturer, such as by pushing the software updates over a publicly available network, so that IVD devices can constantly be up-to-date and can be updated as appropriate.

Moreover, by relying on a publicly available network to communicate data, the disclosed system enables IVD devices to communicate data in a manner transparent to the user. For example, an IVD device may automatically transmit data, including the results of a diagnostic test and any additional data appropriate for the test, to a remote network element by automatically establishing a connection with the publicly accessible network and by automatically communicating the appropriate information to the remote location. In various embodiments, such communication enables IVD devices to communicate test results and other data to a network database server and/or to other IVD devices, forming an ad-hoc network of IVD devices. In another embodiment, the data communicated from an IVD device can be automatically communicated to an appropriate handheld destination, such as an appropriate handheld device of a medical professional or other health care personnel.

In one embodiment, as discussed above, an IVD device is configured to upload data to one or more database servers. In this embodiment, the database servers may be configured to archive test results, aggregate test results into summary reports, or analyze test results for spatial, temporal, or other correlations. These database servers may additionally be configured to perform other analyses on the data, as appropriate, depending upon the type of data uploaded and the goals of the parties managing and implementing the database servers. These database servers may, in various embodiments, be maintained by device manufacturers responsible for manufacture of the IVD devices. In these embodiments, the database servers may correspond to device manufacturer computers 212 in FIG. 2.

The ability of IVD devices to upload data directly to database servers results in a number of advantages of the disclosed system. First, patient care facilities can obtain test results from database servers through secure Internet or other network connections and store the retrieved results in their own databases (e.g., their own HIS or LIS databases). Thus, the installation effort for a patient care facility can be reduced to setting up hardware and software internal to the patient care facility to facilitate access of the database server. In addition, the aggregated test reports available due to the processing of the database servers are of value to public health agencies like the CDC, FDA, and WHO. Such reports can be provided in real-time due to the ability of the disclosed IVD devices to directly and automatically communicate diagnostic test result data to database servers.

The ability of IVD devices to connect directly to database servers through a publicly available network also advantageously enables spatial, temporal, or other correlations determined within the test data to improve the specificity of test results. For example, a database server in one embodiment determines one or more correlations within the test data, and can develop or refine a detection algorithm based on the correlations. Due to the network connectivity of the IVD devices, the database server can thereafter push or download the refined algorithm to the IVD devices, as appropriate.

Manufacturers or maintainers of IVD devices can also use the information sent by the IVD devices to database servers to monitor and maintain the health and functionality of the IVD devices. If an IVD device is malfunctioning, the manufacturer can schedule service, download software to remedy the problem, or otherwise deal with the identified problem. The manufacturer or entity responsible for maintain IVD devices can also send control information or data to the various IVD devices to enable those devices to be controlled in a desired way. In addition, the ability of IVD devices to connect to a database server via a publicly available network enables manufacturers to improve the field service and remote diagnosis capabilities of the IVD devices and to manage the inventory and customer base of the IVD devices.

In one embodiment, IVD devices are equipped with the capability of being remotely administrated. For example, if a large number of user errors are detected while performing a particular test by a remote administrator, the disclosed IVD devices can display warning messages and/or lock users from performing one or more functions, including from performing that particular test. Alternatively or in addition, remote administration may be performed on the IVD devices to perform quality control operations. That is, remote administration may track the outcomes of tests, including user errors occurring while performing tests. Various actions, including displaying warning messages, updating IVD devices, or locking users from performing certain functionalities on the IVD devices, may be taken remotely as is appropriate.

Interoperability among the database servers and other elements of the network (including HIS and LIS databases) also enables the network elements to communicate with one another and obtain test information received by each other in real-time. This ability offers the distinct advantage of interoperability among custom database systems through software configuration.

As discussed above, in some embodiments the disclosed IVD devices can communicate with one another via the publicly accessible network disclosed herein. In some embodiments, this communication between IVD devices is referred to as the creation of ad-hoc networks of IVD devices. For example, multiple IVD devices can exchange test results to explore correlations therebetween, and can appropriately notify patient care personnel of unlikely or outlier results. Among other functionalities, the ability to detect aberrations in data collected by various IVD devices enables medical personnel to quickly and accurately verify test results, verify proper usage of the IVD device, ascertain whether an IVD device is still functioning properly, determine whether an IVD device has malfunctioned, and/or determine whether an IVD device has reached the end of its operable life.

As noted above, the disclosed system is further advantageous in that it enables IVD devices to automatically and instantly send results of tests to PDAs, cellular telephones, portable computers, or other handheld or non-handheld devices which are constantly or nearly constantly monitored by medical personnel. In this way, the disclosed system enables patient care personnel to obtain instant notification as test results become available, and to react with treatment or other appropriate action in a timely fashion.

It should be understood by those skilled in the art that various modifications, combinations, sub-combinations and alterations may occur depending on design requirements and other factors insofar as they are within the scope of the appended claims or the equivalents thereof.

The invention is claimed as follows:

1. A diagnostic test analysis system comprising:
   at least one processor;
   at least one display device;
   at least one network interface device configured to enable access to at least one publicly accessible wireless data network; and
   at least one memory device which stores a plurality of instructions which, when executed by the at least one processor, cause the at least one processor to operate with the at least one display device and the at least one network interface device to:
      determine a raw data result of a diagnostic test based on at least one biological sample provided by a user via a lateral flow assay strip, wherein the raw data result is determined based at least in part on analyzing the lateral flow assay strip, the raw data result comprising a voltage,
      automatically determine additional data based on network information of the publicly accessible wireless data network, hardware information associated with the diagnostic test analysis system, or environmental information associated with an environment in which the diagnostic test was performed,
      store the additional data in association with data indicative of the raw data result of the diagnostic test, and
      automatically send the data indicative of the raw data result of the diagnostic test and the associated additional data to a remote network element via the publicly accessible wireless data network, the remote network element configured to combine the sent data indicative of the result of the diagnostic test and the associated additional data with sent data from a remote in-vitro diagnostic device, and to perform at least one analysis on the combined data based at least in part on the raw data result.

2. The diagnostic test analysis system of claim 1, wherein the plurality of instructions cause the at least one processor to operate with the at least one network interface device to receive the additional data via the publicly accessible wireless network.

3. The diagnostic test analysis system of claim 1, wherein the plurality of instructions cause the at least one processor to operate with the at least one network interface device to receive data indicative of the at least one analysis on the combined data.

4. The diagnostic test analysis system of claim 3, wherein the plurality of instructions cause the at least one processor to determine a second result of a second diagnostic test based, at least in part, on the received data indicative of the at least one analysis on the combined data.

5. The diagnostic test analysis system of claim 3, wherein the at least one analysis on the combined data is performed in real-time.

6. The diagnostic test analysis system of claim 1, wherein the remote network element includes the remote in-vitro diagnostic device.

7. The diagnostic test analysis system of claim 1, wherein the remote network element includes a portable device of a medical professional, the portable device selected from the group consisting of: a personal digital assistant, a notebook computer, a netbook computer, and a mobile telephone.

8. The diagnostic test analysis system of claim 1, wherein the plurality of instructions cause the at least one processor to operate with the at least one network interface device to communicate directly with the remote in-vitro diagnostic device to form an ad-hoc network of devices.

9. A diagnostic test analysis method comprising:
    determining, via a diagnostic test analysis system, a raw data result of a diagnostic test based on at least one biological sample provided by a user via a lateral flow assay strip, wherein the diagnostic test analysis system is configured to analyze the lateral flow assay strip to determine the raw data result, the raw data result comprising a voltage;
    automatically determining additional data based on network information of a publicly accessible wireless data network, hardware information associated with the diagnostic test analysis system, or environmental information associated with an environment in which the diagnostic test was performed;
    storing the additional data in association with data indicative of the raw data result of the diagnostic test; and
    automatically sending the data indicative of the raw data result of the diagnostic test and the associated additional data to a remote network element via the publicly accessible wireless data network, the remote network element configured to combine the sent data indicative of the result of the diagnostic test and the associated additional data with sent data from a remote in-vitro diagnostic device, and to perform at least one analysis on the combined data based at least in part on the raw data result.

10. The diagnostic test analysis method of claim 9, further comprising receiving the additional data via the publicly accessible wireless network.

11. The diagnostic test analysis method of claim 9, further comprising receiving data indicative of the at least one analysis on the combined data.

12. The diagnostic test analysis method of claim 11, further comprising determining a second result of a second diagnostic test based, at least in part, on the received data indicative of the at least one analysis on the combined data.

13. The diagnostic test analysis method of claim 11, wherein the at least one analysis on the combined data is performed in real-time.

14. The diagnostic test analysis method of claim 9, wherein the remote network element includes the remote in-vitro diagnostic device.

15. The diagnostic test analysis method of claim 9, wherein the remote network element includes a portable device of a medical professional, the portable device selected from the group consisting of: a personal digital assistant, a notebook computer, a netbook computer, and a mobile telephone.

16. The diagnostic test analysis method of claim 9, further comprising communicating directly with the remote in-vitro diagnostic device to form an ad-hoc network of devices.

* * * * *